(12) United States Patent
Maruyama (10) Patent No.: US 10,448,646 B2
(45) Date of Patent: *Oct. 22, 2019

(54) ATTRACTING TOOL

(71) Applicant: Kobayashi Pharmaceutical Co., Ltd., Osaka-shi (JP)

(72) Inventor: Tetsuya Maruyama, Ibaraki (JP)

(73) Assignee: Kobayashi Pharmaceutical Co., Ltd., Osaka-shi (JP)

( * ) Notice: Subject to any disclaimer, the term of this patent is extended or adjusted under 35 U.S.C. 154(b) by 691 days.

This patent is subject to a terminal disclaimer.

(21) Appl. No.: 14/908,781

(22) PCT Filed: Jul. 30, 2013

(86) PCT No.: PCT/JP2013/070660
§ 371 (c)(1),
(2) Date: Jan. 29, 2016

(87) PCT Pub. No.: WO2015/015573
PCT Pub. Date: Feb. 5, 2015

(65) Prior Publication Data
US 2016/0174569 A1    Jun. 23, 2016

(51) Int. Cl.
*A01M 31/06* (2006.01)
*A01N 63/02* (2006.01)
*A01M 31/00* (2006.01)
*A01M 1/20* (2006.01)

(52) U.S. Cl.
CPC ........... *A01N 63/02* (2013.01); *A01M 1/2061* (2013.01); *A01M 31/008* (2013.01); *A01M 31/06* (2013.01)

(58) Field of Classification Search
None
See application file for complete search history.

(56) References Cited

U.S. PATENT DOCUMENTS

| | | | |
|---|---|---|---|
| 3,980,070 | A | 9/1976 | Krupa |
| 4,167,561 | A | 9/1979 | Lamberti et al. |
| 4,771,563 | A | 9/1988 | Easley |
| 5,882,885 | A | 3/1999 | Burnham |
| 9,920,954 | B2* | 3/2018 | Nishioka ............... A61F 7/034 |
| 9,945,584 | B2* | 4/2018 | Yasuda ................. A61F 7/034 |
| 2002/0164483 | A1* | 11/2002 | Mercuri ................. B32B 18/00 428/408 |
| 2003/0037476 | A1* | 2/2003 | Peavy ................ A01M 31/008 43/1 |
| 2004/0042965 | A1 | 3/2004 | Usui et al. |
| 2004/0149732 | A1* | 8/2004 | Usui ...................... A61F 7/034 219/528 |
| 2006/0154006 | A1 | 7/2006 | Usui et al. |
| 2008/0206549 | A1 | 8/2008 | Dodo |
| 2008/0273913 | A1* | 11/2008 | Austreng ............ A01M 31/008 401/118 |
| 2009/0277973 | A1 | 11/2009 | Kennon |
| 2010/0063640 | A1 | 3/2010 | Olmstead |
| 2013/0008425 | A1* | 1/2013 | Matsuo ................... A61F 7/034 126/204 |
| 2015/0211766 | A1 | 7/2015 | Yasuda et al. |
| 2016/0174569 | A1 | 6/2016 | Maruyama |

FOREIGN PATENT DOCUMENTS

| | | |
|---|---|---|
| CN | 1181482 A | 5/1998 |
| CN | 1230670 A | 10/1999 |
| CN | 1378433 A | 11/2002 |
| CN | 101338182 A | 1/2009 |
| CN | 102492401 A | 6/2012 |
| JP | 57-8726 A | 1/1982 |
| JP | 57-119753 A | 7/1982 |
| JP | 63-143171 U | 9/1988 |
| JP | 05-194952 A | 8/1993 |
| JP | 05-279595 A | 10/1993 |
| JP | 06-064912 A | 3/1994 |
| JP | 11-049627 A | 2/1999 |
| JP | 11-137275 A | 5/1999 |
| JP | 11-181433 A | 7/1999 |
| JP | 2000-060887 A | 2/2000 |
| JP | 2001-137273 A | 5/2001 |
| JP | 2001-137275 A | 5/2001 |
| JP | 2001-212166 A | 8/2001 |
| JP | 2001-218816 A | 8/2001 |
| JP | 2002-155273 A | 5/2002 |
| JP | 2002-204833 A | 7/2002 |
| JP | 2003-129041 A | 5/2003 |
| JP | 2004-065949 A | 3/2004 |
| JP | 2004-073828 A | 3/2004 |
| JP | 2004-180959 A | 7/2004 |
| JP | 2006-223851 A | 8/2006 |
| JP | 2007-154105 A | 6/2007 |
| JP | 4093348 B2 | 6/2008 |
| JP | 2009-035723 A | 2/2009 |
| JP | 2009-062250 A | 3/2009 |
| JP | 2010-022405 A | 2/2010 |
| JP | 2010-051690 A | 3/2010 |
| JP | 2011-160885 A | 8/2011 |
| JP | 2012-140537 A | 7/2012 |

(Continued)

OTHER PUBLICATIONS

English Translation of International Preliminary Report on Patentability Chapter I (IB/373).
International Search Report dated Oct. 29, 2013, issued for PCT/JP2013/070660.
International Search Report dated Sep. 10, 2013, issued for PCT/JP2013/070497.
Supplementary European Search Report dated Mar. 15, 2016, issued for the European patent application No. 13825934.6.

(Continued)

*Primary Examiner* — Robert T. Crow
*Assistant Examiner* — John P Nguyen
(74) *Attorney, Agent, or Firm* — Locke Lord LLP; James E. Armstrong, IV; Nicholas J. DiCeglie, Jr.

(57) ABSTRACT

The present invention provides an attracting tool that is convenient, inexpensive, and useful for hunting. The present invention provides an attracting tool comprising an exothermic composition and an attractant, the exothermic composition containing an oxidation accelerator having an iodine adsorption number of not more than 700 g/kg, an oxidizable metal powder, and water, wherein at least the exothermic composition is housed in an air-permeable container bag.

17 Claims, 1 Drawing Sheet

(56) References Cited

FOREIGN PATENT DOCUMENTS

| WO | 01/26528 A1 | 4/2001 |
|---|---|---|
| WO | 2006/006656 A1 | 1/2006 |
| WO | 2009/156907 A2 | 12/2009 |

OTHER PUBLICATIONS

Office Action dated May 31, 2016, issued for the corresponding JP patent application No. 2012-171066 and English translation thereof.
Office Action dated Jan. 4, 2017 for JP patent application No. 2012-171066 and English translation thereof.
Office Action dated Nov. 27, 2015 for CN Patent Application No. 201380051644.7.
International Search Report dated Feb. 26, 2013, issued for PCT/JP2013/052177.
Supplementary European Search Report dated Oct. 6, 2015 for EP Patent Application No. 13743049.2.
Office Action issued in corresponding Japanese Patent Application No. JP 2013-015526, dated Aug. 1, 2017.
Adsorption of Iodine by Carbon Black (2), Nippon Gomu Kyokaishi, 1962, vol. 35, No. 8, pp. 578-582.
Carbonization and activation techniques for production of carbonaceous adsorbent, Tanso, 2004, No. 211, pp. 21-29.

* cited by examiner

ATTRACTING TOOL

TECHNICAL FIELD

The present invention relates to an attracting tool.

BACKGROUND ART

There are many known hunting tools. For example, when birds and wild animals are the target of hunting, a device that diffuses an attractant around the target area has been known as a tool using the characteristics that birds and wild animals are attracted to certain attractants. Examples of this device, such as a device for spraying an attractant automatically on a schedule (Patent Document 1), and a device for spraying a heated attractant (Patent Documents 2 and 3), have been reported.

However, these devices have several inconveniences including the trouble of attaching an attractant to the device, or adherence of the attractant to skin or clothing when the attractant is attached to the device. Further, they also have other drawbacks such as a relatively high cost for the container for spraying an attractant, and bulkiness of the device.

In view of the above problems, it is important to provide a tool that is convenient, inexpensive, and useful for hunting.

CITATION LIST

Patent Documents

Patent Document 1: Specification of US Patent Application Publication No. 2010/0063640
Patent Document 2: Specification of US Patent Application Publication No. 2009/0277973
Patent Document 3: Specification of U.S. Pat. No. 4,771,563

SUMMARY OF INVENTION

Technical Problem

An object of the present invention is to provide an attracting tool that is convenient, inexpensive, and useful for hunting.

Solution to Problem

The present inventors have conducted extensive research to solve the above problems, and found that by using an attracting tool containing an exothermic composition containing an oxidation accelerator having an iodine adsorption number of not more than 700 g/kg and an attractant, it is possible to effectively diffuse an attractant from the attracting tool even when the exothermic composition and the attractant coexist in contact with each other. The present invention was accomplished by conducting further research based on this finding.

More specifically, the present invention provides the following inventions.

Item 1. An attracting tool comprising an exothermic composition and an attractant, the exothermic composition containing an oxidation accelerator having an iodine adsorption number of not more than 700 g/kg, an oxidizable metal powder and water, wherein at least the exothermic composition is housed in an air-permeable container bag.

Item 2. The attracting tool according to Item 1, wherein the attracting tool is used for attracting animals.

Item 3. The attracting tool according to Item 1 or 2, wherein the exothermic composition further contains a water-soluble salt, a water-retaining agent, and/or a metal ion sequestrant.

Item 4. The attracting tool according to any one of Items 1 to 3, wherein the proportion of the oxidation accelerator in the exothermic composition is 1 to 30 wt %.

Item 5. The attracting tool according to any one of Items 1 to 4, wherein the attractant is contained in an amount of 0.1 to 25 parts by weight per 100 parts by weight of the exothermic composition.

Item 6. The attracting tool according to any one of Items 1 to 5, wherein the attractant is contained in an amount of 0.1 to 500 parts by weight per 100 parts by weight of the oxidation accelerator in the exothermic composition.

Item 7. The attracting tool according to any one of Items 1 to 6, wherein the oxidation accelerator is at least one member selected from the group consisting of carbon black, graphite, activated carbon, coal, charcoal, bamboo charcoal, acetylene black, and waste coffee grounds charcoal.

Item 8. The attracting tool according to any one of Items 1 to 7, wherein the oxidation accelerator has an iodine adsorption number of not more than 500 g/kg.

Item 9. The attracting tool according to any one of Items 1 to 8, wherein the oxidation accelerator has electrical conductivity.

Item 10. The attracting tool according to any one of Items 1 to 9, wherein the attracting tool comprises an exothermic composition containing an oxidation accelerator having an iodine adsorption number of not more than 700 g/kg and electrical conductivity, an oxidizable metal powder, water, a water-soluble salt, and a water-retaining agent; and an attractant.

Item 11. The attracting tool according to any one of Items 1 to 10, wherein the attracting tool comprises an exothermic composition containing an oxidation accelerator having an iodine adsorption number of not more than 700 g/kg and electrical conductivity, an oxidizable metal powder, water, a water-soluble salt, a water-retaining agent, and a metal ion sequestrant; and an attractant.

Item 12. The attracting tool according to any one of Items 1 to 11, wherein the attractant is housed in an air-permeable container bag.

Item 13. The attracting tool according to any one of Items 1 to 12, wherein the attractant is supported on a carrier.

Item 14. The attracting tool according to any one of Items 1 to 13, wherein the container bag is biodegradable and/or contains an oxidative degradation agent.

Item 15. A method for attracting an animal, comprising the step of disposing the attracting tool according to any one of Items 1 to 14 in a target area.

Item 16. A method for producing an attracting tool with improved attractant diffusion, comprising the step of combining an oxidation accelerator having an iodine adsorption number of not more than 700 g/kg, an oxidizable metal powder, water, and an attractant.

Item 17. A method for improving attractant diffusion of an attracting tool, comprising the step of combining an oxidation accelerator having an iodine adsorption number of not more than 700 g/kg, an oxidizable metal powder, water, and an attractant.

Item 18. A method for improving attractant diffusion of an attracting tool comprising an attractant by using an exothermic composition containing an oxidation accelerator having an iodine adsorption number of not more than 700 g/kg, an oxidizable metal powder, and water.

Item 19. The method according to any one of Items 16 to 18, wherein the attractant, the attracting tool, and/or the exothermic composition have the characteristics described in any one of Items 1 to 14.

Item 20. Use of an exothermic composition comprising an oxidation accelerator having an iodine adsorption number of not more than 700 g/kg, an oxidizable metal powder, and water, for the production of an attracting tool comprising an attractant.

Item 21. Use of an exothermic composition comprising an oxidation accelerator having an iodine adsorption number of not more than 700 g/kg, an oxidizable metal powder, and water, for improving attractant diffusion of an attracting tool comprising an attractant.

Item 22. The use according to Item 20 or 21, wherein the attractant, the attracting tool, and/or the exothermic composition have the characteristics described in any one of Items 1 to 14.

Advantageous Effects of Invention

The attracting tool of the present invention exhibits excellent attraction effects as it contains an oxidation accelerator having an iodine adsorption number of not more than 700 g/kg. In particular, the attracting tool of the present invention is capable of effectively diffusing an attractant even when the exothermic composition containing an oxidation accelerator having an iodine adsorption number of not more than 700 g/kg and the attractant coexist in contact with each other, thereby exhibiting desirable attraction effects. Further, the attracting tool of the present invention is capable of further effectively diffusing an attractant due to its exothermic property. Moreover, the attracting tool of the present invention is capable of effectively diffusing an attractant even when a certain period of time has passed after the beginning of use, not to mention immediately after the beginning of use. Further, the attracting tool of the present invention is capable of effectively diffusing an attractant even when the attracting tool is used after the elapse of a certain period of time after the production. As is clear from the above, the attracting tool of the present invention has an improved attractant diffusion ability, thereby efficiently exhibiting attraction effects.

Further, the attracting tool of the present invention has no restriction on the type of the attractant; thus, a wide range of desired attractants may be used.

Further, when the container bag for housing the attracting tool of the present invention is biodegradable, it is possible to avoid the trouble of collecting the attracting tool after use, and reduce adverse effects on the environment. The attracting tool of the present invention is also convenient in this point.

Furthermore, the attracting tool of the present invention contains an attractant in a ready-to-use state; thus, for example, the trouble of adding an attractant to the device at the time of use is unnecessary in the attracting tool of the present invention, and the attracting tool of the present invention therefore does not cause inconveniences such as adherence of the attractant to skin or clothing upon the addition. Further, since the container bag for housing the attracting tool of the present invention is inexpensive, the cost of the attracting tool, as well as the bulkiness thereof, is low.

BRIEF DESCRIPTION OF DRAWINGS

In FIG. 3, the attractant is present in an adhesive component.

DESCRIPTION OF EMBODIMENTS

The attracting tool of the present invention has a feature in that it comprises an exothermic composition containing an oxidation accelerator having an iodine adsorption number of not more than 700 g/kg, an oxidizable metal powder, and water; and an attractant, and that at least the exothermic composition is housed in an air-permeable container bag. The attracting tool of the present invention is described below. In this specification, the terms "comprise," "comprising," "contain," and "containing" also include both the meanings of "consist essentially of" and "consist of."

Exothermic Composition

The attracting tool of the present invention comprises an exothermic composition. The exothermic composition generates heat in the presence of oxygen, and contains an oxidation accelerator having an iodine adsorption number of not more than 700 g/kg, an oxidizable metal powder and water.

Herein, any oxidation accelerator having an iodine adsorption number of not more than 700 g/kg may be used. The oxidation accelerator is used for the purpose of promoting the supply of oxygen to the exothermic composition, especially to the oxidizable metal powder, by drawing in air. The iodine adsorption number of the oxidation accelerator is preferably not more than 500 g/kg, more preferably not more than 300 g/kg, further preferably not more than 160 g/kg, particularly preferably not more than 100 g/kg, and further particularly preferably not more than 50 g/kg. The lower limit of the iodine adsorption number is not particularly limited, but is theoretically 0 g/kg, for example.

Examples of the oxidation accelerator include, but not limited thereto as long as the-above mentioned conditions are met and desired effects are obtained, carbon black, graphite, activated carbon, coal, charcoal, bamboo charcoal, acetylene black, and waste coffee grounds charcoal. The oxidation accelerator is preferably carbon black, activated carbon, or charcoal, and more preferably carbon black. These may be used alone or in a combination of two or more. When two or more kinds are used in combination, the iodine adsorption number of the combination (e.g., mixture) preferably satisfies the above-mentioned values. The iodine adsorption number of the respective components can be easily known by a person of skill in the art, and the iodine adsorption number is measured and calculated by the method defined in ASTM D-1510.

The attracting tool of the present invention may generate heat so that the attractant is effectively diffused. The temperature is, for example, about 32 to 85° C., and more preferably about 40 to 70° C. (measurement value based on JIS S4100 (2007)). To allow the attracting tool to further efficiently generate heat to a more preferable temperature, the oxidation accelerator preferably has electrical conductivity. Oxidation accelerators having or not having electrical conductivity are known. Examples of known oxidation accelerators having electrical conductivity equal to or higher than a certain level include, but are not limited to, carbon black, graphite, activated carbon, and the like.

In the present invention, the heat-generation temperature of the attracting tool is measured according to JIS S4100 (2007). More specifically, predetermined underlay material and covering material are laid on a warming portion defined in JIS S4100 (2007). The warming portion is heated to 30° C., and held within one degree of that temperature. Meanwhile, the attracting tool left for 2 or more hours in an atmosphere having the same temperature as the ambient temperature is caused to generate heat based on the method of use. In accordance with a predetermined method, measurement is performed by measuring the time etc. required from the start of heat generation to returning to a predetermined temperature after exceeding the predetermined temperature and reaching the maximum temperature.

Although not limited as long as the desired effects are obtained, for example, from the standpoint of efficiency in the supply of oxygen to the attracting tool, the oxidation accelerator is preferably in a form such as powdery, granular, or fibrous. These may be used alone or in a combination of two or more, and the average particle diameter of the oxidation accelerator is, for example, 0.001 to 1000 μm, preferably 0.005 to 500 μm, and more preferably 0.01 to 200 μm.

The amount of the oxidation accelerator is not limited as long as the desired effects are obtained. The proportion of the oxidation accelerator in the exothermic composition is, for example, 1 to 30 wt %, preferably 3 to 25 wt %, and more preferably 5 to 23 wt %.

The amount of the oxidation accelerator relative to the oxidizable metal powder described later is also not limited as long as the desired effects are obtained. The amount of the oxidation accelerator per 100 parts by weight of the oxidizable metal powder is, for example, 2 to 60 parts by weight, preferably 5 to 50 parts by weight, and more preferably 9 to 40 parts by weight.

The oxidizable metal powder contained in the exothermic composition is not limited as long as it is a metallic powder which generates heat when being oxidized. Examples thereof include iron powder, zinc powder, aluminum powder, magnesium powder, and copper powder. A preferable example is iron powder. Examples of the iron powder include reduced iron powder, cast-iron powder, atomized iron powder, and electrolytic-iron powder. These may be used alone, or in a combination of two or more.

The oxidizable metal powder may be powdery, granular, or fibrous, and these may be used alone or in a combination of two or more.

Although not limited as long as the desired effects are obtained, from the standpoint of heat generation efficiency etc., an example of the average particle diameter of oxidizable metal powder is 0.01 to 1000 μm, preferably 0.1 to 500 μm, and more preferably 0.5 to 300 μm. The average particle diameter of oxidizable metal powder can be measured, for example, by a JIS method using a standard sieve.

The amount of the oxidizable metal powder is not limited as long as the desired effects are obtained. The proportion of the oxidizable metal powder in the exothermic composition is, for example, 20 to 80 wt %, preferably 40 to 75 wt %, and more preferably 45 to 70 wt %.

Usable water includes distilled water, tap water, ion exchange water, pure water, ultrapure water, industrial water, and the like.

The amount of water is also not limited as long as the desired effects are obtained. The proportion of water in the exothermic composition is, for example, 1 to 60 wt %, preferably 3 to 40 wt %, and more preferably 5 to 35 wt %.

In addition to the above-mentioned components, at least one substance selected from the group consisting of water-soluble salts, water-retaining agents and metal ion sequestrants may be further blended in the exothermic composition if necessary.

The water-soluble salts contained in the exothermic composition are blended in order to promote the oxidation of the oxidizable metal powder, and are not limited as long as the desired effects are obtained. Preferable examples of the water-soluble salts include chlorides and sulfates of alkali metals such as sodium and potassium; chlorides and sulfates of alkaline earth metals such as calcium and magnesium; and chlorides and sulfates of metals such as iron, copper, aluminum, zinc, nickel, silver, and barium. More preferable examples thereof include potassium chloride, sodium chloride, and the like. In particular, potassium chloride, sodium chloride and the like are suitable for a biodegradable attracting tool. These may be used alone, or in a combination of two or more.

The amount of water-soluble salt is also not limited as long as the desired effects are obtained. The proportion of the water-soluble salt in the exothermic composition is, for example, 0.1 to 20 wt %, preferably 0.1 to 10 wt %, more preferably 0.5 to 10 wt %, further preferably 0.5 to 7 wt %, particularly preferably 1 to 5 wt %.

The water-retaining agent has a function of retaining water, and is not limited as long as it has the function and can produce desired effects. Examples thereof include porous substances, water-absorbing resins, and the like. Examples of the water-retaining agent include natural and synthetic inorganic substances such as vermiculite, perlite, calcium silicate, kaolin, talc, smectite, mica, bentonite, calcium carbonate, silica gel, alumina, zeolite, silicon dioxide, diatomaceous earth and aluminum oxide; and natural and synthetic organic substances such as pulp, wood flour (sawdust), cotton, polyacrylate-based resins, polysulfonate-based resins, maleic anhydride salt-based resins, polyacrylamide-based resins, polyvinyl alcohol-based resins, polyethylene oxide-based resins, polyaspartate-based resins, polyglutamate-based resins, poly alginate-based resins, starches, and cellulose. Preferable examples thereof include vermiculite, perlite, silica gel, diatomaceous earth, aluminum oxide, wood flour (sawdust), pulp, and polyacrylate-based resins. More preferable examples thereof include vermiculite and polyacrylate-based resins. These may be used alone, or in a combination of two or more.

Although not limited as long as the desired effects are obtained, an example of the average particle diameter of the water-retaining agent is 0.1 to 3000 μm, preferably 0.5 to 1000 μm, and more preferably 1 to 500 μm. The average particle diameter of the water-retaining agent is also measured in a manner similar to the aforementioned method for measuring that of the oxidizable metal powder.

The amount of the water-retaining agent is also not limited as long as the desired effects are obtained. The proportion of the water-retaining agent in the exothermic composition is, for example, 1 to 20 wt %, preferably 2 to 15 wt %, and more preferably 3 to 10 wt %.

In these water-retaining agents, water-retaining agents having a porous structure, especially vermiculite etc., can serve not only as a water-retaining agent but also as an air passageway.

The metal ion sequestrant is not limited as long as it is a substance having an ability to sequester metal ions. Examples include a substance with two or more coordinations and having an ability to bind to metal ions by the ligand, a substance having an ability to electrically adsorb metal ions, a substance having an ability to physically adsorb metal ions in the micropores, a substance having an ability to sequester metal ions, and combinations of these substances. Known metal ion sequestrants are one example of these substances. Examples include metal ion sequestrants such as aminocarboxylic acid-based metal ion sequestrants, e.g., ethylenediaminetetraacetic acid, nitrilotriacetic acid, diethylenetriaminepentaacetic acid, hydroxyethylenediaminetetraacetic acid, hydroxyethylenediaminetriacetic acid, triethylenetetraminehexaacetic acid, 1,3-propanediaminetetraacetic acid, 1,3-diamino-2-hydroxypropane tetraacetic acid, hydroxyethyliminodiacetic acid, glycol etherdiaminetetraacetic acid, dicarboxymethylglutamic acid, and salts thereof; phosphonic acid-based metal ion sequestrants, such as hydroxyethylidenediphosphonic acid, nitrilotris methylenephosphonic acid, phosphonobutanetricarboxylic acid, ethylenediaminetetramethylene phosphonic acid, diethylenetriaminepentamethylene phosphonic acid, and salts thereof; condensed phosphoric acid-based metal ion sequestrants, such as tripolyphosphoric acid, pyrophosphoric acid, metaphosphoric acid, and salts thereof; carboxylic acid-based metal ion sequestrants, such as dihydroxyglycine, dihydroxyethylglycine, citric acid, succinic acid, malic acid, fumaric acid, tartaric acid, malonic acid, maleic acid, ascorbic acid, gluconic acid, and salts thereof; and various substances having an ability to adsorb metal ions, such as zeolite (aluminosilicate), acrylic acid, methacrylic acid, bipyridine, phenanthroline, porphyrin, phthalocyanine, corrole, chlorin, and crown ether. Examples of these salts include known salts such as salts of alkali metals, e.g., sodium and potassium; salts of alkaline earth metals, such as magnesium and calcium; ammonium salts; and amine salts.

As a metal ion sequestrant, it is preferable to use aminocarboxylic acid-based metal ion sequestrants, condensed phosphoric acid-based metal ion sequestrants, and carboxylic acid-based metal ion sequestrants, and it is more preferable to use aminocarboxylic acid-based metal ion sequestrants and carboxylic acid-based metal ion sequestrants.

Of these, as metal ion sequestrants, it is furthermore preferable to use ethylenediaminetetraacetic acid, nitrilotriacetic acid, tripolyphosphoric acid, pyrophosphoric acid, citric acid, malic acid, and salts thereof, and it is particularly preferable to use ethylenediaminetetraacetic acid, citric acid, and salts thereof.

These may be used singly, or in a combination of two or more.

The amount of the metal ion sequestrant is not limited as long as the desired effects are obtained. The proportion of the metal ion sequestrant in the exothermic composition is, for example, 0.0001 to 10 wt %, preferably 0.001 to 7 wt %, and more preferably 0.01 to 5 wt %.

The amount of the metal ion sequestrant is not limited as long as the desired effects are obtained. The amount of the metal ion sequestrant contained in the exothermic composition is, for example, 0.0002 to 20 parts by weight, preferably 0.002 to 15 parts by weight, and more preferably 0.02 to 10 parts by weight, per 100 parts by weight of the oxidizable metal powder.

Further, when the attracting tool of the present invention contains a metal ion sequestrant, in order to more effectively exhibit the sequestering effects, it is preferable to dissolve the metal ion sequestrant in water beforehand to allow the metal ion sequestrant to be supported on at least one of the components other than the oxidizable metal powder contained in the exothermic composition by impregnation or the like.

In addition to the components mentioned above, the exothermic composition may further optionally contain other components that can be contained in an exothermic composition. Examples of such components include, but are not limited to, surfactants, hydrogen-generating inhibitors, thickening agents, and excipients.

In such an attracting tool of the present invention, containing activated carbon is not excluded as long as the desired effects are obtained. From the standpoint of further reducing or preventing the loss of attraction effects of the attracting tool, it is preferable to use a small amount of activated carbon that has been used in known products to an extent in which the attraction effects are not lost, or does not use activated carbon.

In the exothermic composition, the total amount of the oxidation accelerator having an iodine adsorption number of not more than 700 g/kg, the oxidizable metal powder, and water is not limited as long as the desired effects are obtained, and may be suitably set so that a heat generation temperature of the exothermic composition becomes a preferable temperature (e.g., about 32 to 85° C., more preferably about 40 to 70° C., measurement value according to JIS S4100) for an attracting tool. Further, when the exothermic composition further contains at least one member selected from the group consisting of water-soluble salts, water-retaining agents, and metal ion sequestrants, the total amount of these components is not limited as long as the desired effects are obtained, and may be suitably set so that a heat generation temperature of the exothermic composition becomes a preferable temperature for an attracting tool.

As an embodiment of the exothermic composition used for the attracting tool of the present invention, the amounts of the components in the exothermic composition are, for example, as follows: 1 to 30 wt % for the oxidation accelerator, 20 to 80 wt % for the oxidizable metal powder, and 1 to 50 wt % for water.

As another embodiment of the exothermic composition used for the attracting tool of the present invention, the amounts of the components in the exothermic composition are, for example, as follows: 1 to 30 wt % for the oxidation accelerator, 20 to 80 wt % for the oxidizable metal powder, 0.1 to 10 wt for the water-soluble salt, and 1 to 50 wt % for water.

As another embodiment of the exothermic composition used for the attracting tool of the present invention, the amounts of the components in the exothermic composition are, for example, as follows: 1 to 30 wt % for the oxidation accelerator, 20 to 80 wt % for the oxidizable metal powder, 1 to 20 wt % for the water-retaining agent, and 1 to 50 wt % for water.

As another embodiment of the exothermic composition used for the attracting tool of the present invention, the amounts of the components in the exothermic composition are, for example, as follows: 1 to 30 wt % for the oxidation accelerator, 20 to 80 wt % for the oxidizable metal powder, 0.1 to 10 wt % for the water-soluble salt, 1 to 20 wt % for the water-retaining agent, and 1 to 50 wt % for water.

As another embodiment of the exothermic composition used for the attracting tool of the present invention, the amounts of the components in the exothermic composition are, for example, as follows: 1 to 30 wt % for the oxidation accelerator, 20 to 80 wt % for the oxidizable metal powder, 0.1 to 20 wt % for the water-soluble salt, 1 to 20 wt % for the water-retaining agent, 0.0001 to 10 wt % for the metal ion sequestrant, and 1 to 60 wt % for water.

An example of another embodiment of the exothermic composition used for the attracting tool of the present invention is a composition containing carbon black having an iodine adsorption number of not more than 700 g/kg, iron powder, and water. An example of another embodiment of the exothermic composition used for the attracting tool of the present invention is a composition containing carbon black having an iodine adsorption number of not more than 700 g/kg, iron powder, sodium chloride and/or potassium chloride, and water. An example of another embodiment of the exothermic composition used for the attracting tool of the present invention is a composition containing carbon black having an iodine adsorption number of not more than 700 g/kg, iron powder, a water-absorbing resin and/or vermiculite, and water. An example of another embodiment of the exothermic composition used for the attracting tool of the present invention is a composition containing carbon black having an iodine adsorption number of not more than 700 g/kg, iron powder, sodium chloride and/or potassium chloride, a water-absorbing resin and/or vermiculite, and water. An example of another embodiment of the exothermic composition used for the attracting tool of the present invention is a composition containing carbon black having an iodine adsorption number of not more than 700 g/kg, iron powder, sodium chloride and/or potassium chloride, a water-absorbing resin and/or vermiculite, ethylenediaminetetraacetic acid trisodium salt, and water.

In the embodiments described above, the oxidation accelerator preferably has an iodine adsorption number of 0 to 500 g/kg, more preferably 0 to 300 g/kg, further preferably 0 to 160 g/kg, particularly preferably 0 to 100 g/kg, and further particularly preferably 0 to 50 g/kg. In these embodiments, the oxidation accelerator more preferably has electrical conductivity.

The exothermic composition is prepared by mixing the above components. The exothermic composition may be prepared in the presence of oxygen, or may be prepared in vacuum or in an inert gas atmosphere. Known procedures can be used for such preparation.

In the attracting tool of the present invention, as described above, the oxidation accelerator having an iodine adsorption number of not more than 700 g/kg is used. Therefore, by preparing the exothermic composition according to the methods described above, loss of the attraction effects can be reduced or prevented even when an attractant is combined with the exothermic composition. Therefore, the attracting tool of the present invention exhibits attraction effects for a long period of time.

Air-Permeable Container Bag for Housing Exothermic Composition

In the attracting tool of the present invention, the exothermic composition is housed in an air-permeable container bag for housing the exothermic composition (hereinafter may also be referred to as "container bag for the exothermic composition"). The air-permeable container bag for housing the exothermic composition is not limited as long as it can house the exothermic composition, and has air-permeability. Known container bags can be used as the air-permeable container bag for housing the exothermic composition. In view of, for example, preventing leakage of the exothermic composition, imparting durability against the heat generation by the exothermic composition, and improving the ease of use of the attracting tool, air-permeable bags used for known disposable body warmers and the like can be used as the container bag for the exothermic composition, for example.

A more specific example of the container bag for the exothermic composition is, but not limited to, a container bag having a laminated structure in which an air-permeable resin film is laminated on an air-permeable woven or nonwoven fabric. In this case, the air-permeable resin film is arranged on the inside of the container bag for the exothermic composition, and the air-permeable woven or nonwoven fabric is arranged on the outside of the container bag for the exothermic composition.

The resin used for the air-permeable resin film is not particularly limited; preferable examples thereof include thermoplastic resins. Examples of the thermoplastic resins include polyethylene, polypropylene and like polyolefin, polyester, polyamide, polyurethane, polystyrene, polyvinyl alcohol, polyvinyl chloride, polyvinylidene chloride, polycarbonate, ethylene-vinyl acetate copolymers, and the like. Preferable examples of the thermoplastic resins include polyolefin, polystyrene, polyvinyl chloride, polyvinylidene chloride, polyamide, ethylene-vinyl acetate copolymers, and like hydrolysis resistant resins. More preferable examples include polyolefin. Particularly preferable examples include polyethylene and polypropylene. Further particularly preferable examples include polyethylene. These resins may be used singly, or in a combination of two or more. In particular, the resins listed above as preferable examples are also preferable in view of their superior biodegradability after use, despite their strength at the time of use.

The air-permeable resin film used in the present invention has pores at least partially, thus ensuring air permeability in the resin film formed of the described resin. The pores allow air to move in and out of the container bag for the exothermic composition. The pores are not limited as long as they are of a size that prevents leakage of the exothermic composition to the outside of the container bag. The size, shape, and number of the pores may be suitably set by a person skilled in the art within a range in which the attracting tool ensures desired effects. Means for forming pores in the resin film are hitherto known; thus, the pore may be formed by known procedures.

Examples of the fiber materials to be used for the air-permeable woven or nonwoven fabric include synthetic fibers such as polyethylene, polypropylene and like polyolefin, nylon, vinylon, polyester, rayon, acrylic, acetate, polyvinyl chloride, and polybutylene terephthalate; natural fibers such as cotton, hemp, silk, and paper; mixed fibers of synthetic fibers and natural fibers; and the like. In view of comfort in use, examples of the fiber materials include polyolefin, nylon, polyester, and the like. In view of superior biodegradability, polyolefin is preferable as a fiber material. These fibers may be used alone, or in a combination of two or more. The woven or nonwoven fabric is not limited as long as the fabric allows air to move in and out of the container bag for the exothermic composition, and can prevent leakage of the exothermic composition to the outside of the container bag. The weight per area of the fabric is, for example, preferably 15 to 70 g/m$^2$.

The laminate of the air-permeable resin film and the air-permeable woven or nonwoven fabric is not limited as long as the resulting laminate is strong enough to serve as a container bag for the exothermic composition, and ensures air permeability. The laminate can be formed by, for example, a lamination method. Examples of the lamination method include a lamination method using thermal bond, and a lamination method using adhesives such as hot-melt adhesives, acrylic-based adhesives, or urethane-based adhesives. The laminates formed by these methods may be formed partially or entirely on the surface of the container bag for the exothermic composition, as long as the desired effects are obtained.

Commercially available products may be used as the container bag for the exothermic composition.

The size and shape of the container bag for the exothermic composition are also not limited as long as the desired effects are obtained, and may be suitably determined depending on the purpose of use.

Further, for example, when the attracting tool of the present invention is to be used by being fixed to a place, such as a tree, an adhesive sheet may be provided on the outside of the container bag for the exothermic composition of the attracting tool of the present invention. Examples of such an adhesive sheet include known adhesive sheets used for so-called stick-on type disposable warmers to be used by being attached to clothing or the like. An optional adhesive component may be provided on the outside of the container bag for the exothermic composition used for the attracting tool of the present invention as necessary. Further, a hook or the like may be attached to the attracting tool of the present invention, as necessary.

Further, to impart superior biodegradability to the container bag for the exothermic composition, the container bag preferably further contains an oxidative degradation agent (may also be referred to as a chemical degradation agent). By incorporating an oxidative degradation agent, even when the container bag is formed of a material that cannot be naturally degraded, it is possible to decrease the molecular weight of the material after use through oxidative degradation, thereby subjecting the material to microorganism degradation. Further, in the attracting tool of the present invention, if the oxidative degradation agent contained in the container bag and the potassium chloride and/or sodium chloride contained in the exothermic composition coexist, the rapidity of the degradation of the used container bag significantly increases.

In the present invention, the incorporation form of the oxidative degradation agent is not particularly limited insofar as the oxidative degradation agent is contained in the container bag. For example, when the container bag is a laminate made of an air-permeable resin film and woven or non-woven fabric, it is sufficient that at least one of the air-permeable resin film and woven or non-woven fabric contains an oxidative degradation agent. In view of further improving biodegradability after use, it is preferable that both the air-permeable resin film and the woven or non-woven fabric contain an oxidative degradation agent.

In the present invention, an oxidative degradation agent refers to a substance capable of degrading the material of the container bag to a low-molecular-weight material through oxidative degradation to an extent in which the material can be subjected to microorganism degradation. Such oxidative degradation agents are known in this field, and examples thereof are disclosed, for example, in JP2011-212170. Examples of oxidative degradation agents include carboxylic acid metal salts, hydroxycarboxylic acids, transition metal compounds, rare-earth compounds, aromatic ketones, and the like. Other usable oxidative degradation agents include combinations of carboxylic acid metal salts and hydroxycarboxylic acids, combinations of carboxylic acid metal salts and fillers. In the present invention, these oxidative degradation agents may be used alone, or in a combination of two or more.

As examples of the carboxylic acid metal salt used as the oxidative degradation agent, metal salts of aliphatic carboxylic acids having 10 to 20 carbon atoms are preferable, and metal stearate is more preferable. Examples of metal atom constituting the carboxylic acid metal salt include cobalt, cerium, iron, aluminum, antimony, barium, bismuth, cadmium, chromium, copper, gallium, lanthanum, lead, lithium, magnesium, mercury, molybdenum, nickel, calcium, rare earth, silver, sodium, strontium, tin, tungsten, vanadium, yttrium, zinc, zirconium, and the like. Stearates of metals such as cobalt, cerium, and iron are preferable as a carboxylic acid metal salt used as an oxidative degradation agent.

Examples of the hydroxycarboxylic acid used as an oxidative degradation agent include monohydroxy tricarboxylic acids such as citric acid; polyhydroxy dicarboxylic acids such as trihydroxy glutaric acid and saccharic acid; dihydroxydicarboxylic acids such as tartaric acid; monohydroxydicarboxylic acids such as tartronic acid and malic acid; polyhydroxy monocarboxylic acids such as erythric acid, arabic acid, and mannitic acid; and dihydroxymonocarboxylic acids such as glyoxylic acid and glyceric acid.

These carboxylic acid metal salts and hydroxycarboxylic acids can be used alone, or in a combination of two or more.

Examples of the filler that can be used as a component of the oxidative degradation agent include inorganic carbonate, synthetic carbonate, nepheline syenite, talc, magnesium hydroxide, aluminum hydroxide, diatomaceous earth, natural or synthetic silica, calcined clay, and the like. It is desirable that these fillers have a particle diameter of less than 150 meshes. The fillers can be used alone, or in a combination of two or more.

Examples of the transition metal compound used as an oxidative degradation agent include salts of cobalt or magnesium, preferably aliphatic carboxylic acid (C12 to C20) salts of cobalt or magnesium, and more preferably cobalt stearate, cobalt oleate, magnesium stearate, and magnesium oleate. These transition metal compounds can be used alone, or in a combination of two or more.

Examples of rare-earth compounds used as an oxidative degradation agent include rare earths belonging to periodic table Group 3A, and oxides thereof. Specific examples include cerium (Ce), yttrium (Y), neodymium (Nd), rare-earth oxides, hydroxides, rare-earth sulfates, rare-earth nitrates, rare-earth acetates, rare-earth chlorides, rare-earth carboxylates, and the like. More specific examples thereof include cerium oxide, ceric sulfate, ceric ammonium sulfate, ceric ammonium nitrate, cerium acetate, lanthanum nitrate, cerium chloride, cerium nitrate, cerium hydroxide, cerium octylate, lanthanum oxide, yttrium oxide, scandium oxide, and the like. These rare-earth compounds may be used alone, or in a combination of two or more.

Examples of aromatic ketones used as an oxidative degradation agent include benzophenone, anthraquinone, anthrone, acetylbenzophenone, 4-octylbenzophenone, and the like. These aromatic ketones may be used alone, or in a combination of two or more.

In view of further facilitating the biodegradation of the attracting tool of the present invention after use, a combination of a carboxylic acid salt and a rare-earth compound is preferably used as an oxidative degradation agent. A preferable example of an oxidative degradation agent used in the present invention is "P-Life" (produced by P-Life Japan Inc.).

An oxidative degradation agent generally oxidatively degrades, under the action of light, heat, air, etc., a polymer that forms a resin molded body, thereby depolymerizing the polymer to an extent in which microbial degradation can be carried out. In the present invention, among oxidative degradation agents, an oxidative degradation agent that exhibits its effects on oxidative degradation of a polymer upon exposure to light (ultraviolet light) (this oxidative degradation agent is hereinafter referred to as a "light-requiring oxidative degradation agent") is preferably used. Since a container bag containing a light-requiring oxidative degradation agent is not degraded under shaded conditions, by keeping the container bag in a shaded atmosphere (e.g., in a shaded space, a light-resistant container, or a light-proof bag) in the pre-use stage, i.e., during production, distribution, and storage, the container bag can maintain desired functions as a container bag without causing durability deterioration until use. Examples of such light-requiring oxidative degradation agents include an oxidative degradation agent containing a rare-earth compound. More specifically, "P-Life" (trade name, produced by P-Life Japan Inc.) is exemplified.

In the present invention, the proportion of the oxidative degradation agent in the container bag is not limited insofar as the desired effects are obtained. The proportion is suitably determined depending on, for example, the type of the oxidative degradation agent and the type of the material of the container bag. For example, an oxidative degradation agent may be used in an amount of 0.48 to 3.8 mass %, preferably 0.72 to 3.1 mass %, and still more preferably 0.96 to 2.4 mass %, based on the total mass of the container bag.

More specifically, when a container bag is a laminate of an air-permeable resin film and woven or non-woven fabric, an oxidative degradation agent is used, for example, in an amount of 0.4 to 3 mass %, preferably 0.6 to 2.5 mass %, more preferably 0.8 to 2 mass %, based on the total weight of the air-permeable resin film, and in an amount of 0.08 to 0.8 mass %, preferably 0.12 to 0.6 mass %, more preferably 0.16 to 0.4 mass %, based on the total weight of the woven or non-woven fabric.

A container bag containing an oxidative degradation agent can be produced by a known method. For example, the production method below is exemplified: (1) a predetermined amount of oxidative degradation agent is added to a molten resin for forming a container bag, and the molten mixture is formed into pellets; (2) subsequently, the pellets are melted and formed into a material (fiber, film, etc.) for forming a container bag; and (3) the material thus molded into fiber or film is processed into a container bag.

Attractant

The attracting tool of the present invention comprises an attractant. The attractant is not limited, and any arbitrary attractants may be used insofar as they can attract animals. More preferably, the attractant can attract animals as hunting targets, such as birds and wild animals. Examples of attractants include, but are not limited to, urine of animals (at least one animal selected from the group consisting of, for example, deer, reindeer, buffalo, raccoon dog, fox, dog, cat, marten, weasel, mink, bear, palm civet cat, wild boar, squirrel, antelope, nutria, rabbit, coyote, beaver, muskrat, opossum, raccoon, armadillo, and porcupine), artificial urine, animal blood, animal meat juice, plant ground products (cinnamon, *Actinidia polygama*, etc.), flavors (food flavor, etc.), honey, and raw garbage extracts. Since the attraction effects can be enhanced by the heat generated in the attracting tool, an attractant that can vaporize at a temperature (e.g., about 32 to 85° C.) at which the exothermic composition generates heat in the presence of air is more preferable. The attractant may be a liquid, a solid, or in other forms. The attractants exemplified above may be used alone, or in a combination of two or more.

The content of the attractant in the attracting tool of the present invention is not limited as long as the desired effects are obtained. The content of the attractant is, for example, 0.1 to 30 parts by weight, preferably 0.5 to 28 parts by weight, more preferably 2.5 to 25 parts by weight, per 100 parts by weight of the exothermic composition.

Further, the content of the attractant is, for example, 0.1 to 500 parts by weight, preferably 0.5 to 400 parts by weight, more preferably 2.5 to 300 parts by weight, further preferably 12.5 to 200 parts by weight, per 100 parts by weight of the oxidation accelerator having an iodine adsorption number of not more than 700 g/kg contained in the exothermic composition.

The content of the attractant is, for example, 0.1 to 50 parts by weight, preferably 0.5 to 45 parts by weight, more preferably 2.5 to 40 parts by weight, per 100 parts by weight of the oxidizable metal powder contained in the exothermic composition.

Upon incorporation of the attractant in the attracting tool of the present invention, the attractant may also be housed in an air-permeable container bag, or may exist outside the container bag, although it is not limited as long as the attraction effects are ensured.

More specifically, the attractant is incorporated in the attracting tool of the present invention, for example, in a manner such that the attractant coexists with the other components of the exothermic composition and then is housed in the container bag; that the attractant is contained in at least a portion of the container bag for the exothermic composition; or that the attractant is included beforehand in another sheet, an optional adhesive component or the like, or is housed in another air-permeable container bag or the like, and then the sheet, the adhesive component, or another container bag, etc., is disposed inside and/or outside of the container bag for the exothermic composition.

When the attractant coexists with the other components of the exothermic composition, for example, the attractant itself may be mixed with the components; a mixture obtained by mixing an attractant with, for example, water, using a surfactant or the like may be mixed with the components; an attractant or the mixture may be encapsulated beforehand in known microcapsules, and the obtained microcapsules may be mixed with the components; or an attractant or the mixture may be supported on a carrier, and then mixed with the components. In view of preventing adhesion of the attractant to the other components of the exothermic composition as much as possible, and particularly in view of preventing adhesion of the attractant to the oxidation accelerator and the oxidizable metal powder as much as possible, the attractant is, for example, preferably supported on a carrier beforehand, and then mixed with the components. Examples of the carrier include, but not limited to insofar as the effects of the present invention are not impaired, silica, vermiculite, perlite, fluorite, zeolite, fine particle silicon dioxide, pulp, plastics, rubbers, and elastomers. The particle diameter of the carrier is also not limited, insofar as the effects of the present invention are not impaired. An example of the average particle diameter is about 0.1 to 3000 µm, preferably about 0.5 to 1000 µm, more preferably about 1 to 500 µm. The content of the carrier is also not limited insofar as the effects of the present invention are not impaired.

To support the attractant, it is also possible to support the attractant, for example, on the components contained in the exothermic composition. In view of the influence on heat generation, the attractant is preferably supported on components other than the oxidation accelerator and the oxidizable metal powder in the exothermic composition. For example, when the exothermic composition contains a water-retaining agent, the attractant is preferably supported on the water-retaining agent contained in the exothermic composition.

As described above, when the attractant is contained in at least a portion of the container bag for the exothermic composition, the container bag may, for example, be impregnated with the attractant beforehand, or the attractant may be kneaded beforehand into at least one of the film, the woven fabric, and the nonwoven fabric constituting the container bag. As another example, the attractant may be encapsulated in microcapsules, and then the resulting microcapsule may be attached to at least one of the film, woven fabric, and nonwoven fabric constituting the container bag.

Further, as described above, when the attractant is included beforehand in another sheet, an optional adhesive component or the like, or is housed in another air-permeable container bag or the like, and then the sheet, the adhesive component, or another container bag, etc., is disposed inside and/or outside of the container bag for the exothermic composition, examples of the sheet and the adhesive component etc. include known adhesive sheets to be used for so-called stick-on type disposable body warmers, skin-direct stick-on type adhesive sheets, as well as adhesive components and the like to be used for these products. The air-permeable container bag in which the attractant is housed beforehand is, for example, a container bag similar to the aforementioned container bag for the exothermic composition.

The attracting tool of the present invention contains an oxidation accelerator having an iodine adsorption number of not more than 700 g/kg in the exothermic composition; therefore, it is possible to reduce or prevent adsorption of the attractant by the oxidation accelerator. Therefore, as long as the attracting tool is stored without contact with oxygen, it is possible to reduce or prevent the loss of the attractant diffusion property or alteration of the attractant during the storage of the attracting tool, even when the attractant and the exothermic composition exist in contact with each other in the attracting tool of the present invention. Therefore, in the attracting tool of the present invention, it is not essential to dispose the attractant and the exothermic composition so that they do not come into contact with each other.

Attracting Tool

The attracting tool of the present invention comprises the above exothermic composition and the above attractant, and at least the exothermic composition is housed in an air-permeable container bag. The attracting tool of the present invention is produced by housing the exothermic composition prepared in the above manner in the air-permeable container bag described above, adding an attractant in the manner described above, and, as necessary, appropriately adding other arbitrary components.

The thus-produced attracting tool is, in general, further packaged in an air-impermeable outer bag that blocks permeation of oxygen, and is provided or stored in an airtight state. In the attracting tool of the present invention, since the exothermic composition generates heat upon contact with oxygen, it is important to prevent the attracting tool from contacting oxygen during storage to prevent heat generation until usage. Upon usage, the attracting tool of the present invention is used by opening the outer bag, removing the attracting tool from the outer bag, and bringing the exothermic composition into contact with oxygen to generate heat. The outer bag used herein is not particularly limited as long as it is an air-impermeable bag that blocks permeation of oxygen. If the container bag is biodegradable, in particular, if the container bag contains a light-requiring oxidative degradation agent, the outer bag is preferably a light-proof bag.

The attracting tool described above is used by hunters for attracting animals, in particular, hunting animals. The attracting tool diffuses an attractant around the target area, and thereby enables hunters to catch animals using the animal nature of being attracted to an attractant. Therefore, the present invention is more specifically regarded as providing an attracting tool for attracting animals, in particular, hunting animals. The animals are not limited, and hunting animals, in particular, hunting birds and wild animals, are exemplified. Examples include deer, reindeer, buffalo, raccoon dog, fox, dog, cat, marten, weasel, mink, bear, palm civet cat, wild boar, squirrel, antelope, nutria, rabbit, coyote, night heron, duck, Aythya, ptarmigan, quail, goose, copper pheasant, pheasant, bamboo partridge, water hen, snipe, pigeon, bulbul, sparrow, starling, crow, great cormorant, ptarmigan, turkey, beaver, muskrat, opossum, raccoon, armadillo, porcupine, alligator, and snake. Further, the attracting tool of the present invention may be placed and used in an arbitrary manner; for example, the attracting tool may be placed in or attached to a desired place, such as a tree, a rock, or the ground, in the target area. Further, depending on the effects (functions) of the attractant and the effects (functions) of the optional components, the attracting tool of the present invention has additional effects.

The contents of the exothermic composition and the attractant in the attracting tool of the present invention are not limited as long as the desired effects are obtained. However, in view of easy handling and efficient acquisition of the effects, their total amount is, for example, 10 to 150 g, more preferably 15 to 100 g, further preferably 20 to 100 g.

The attracting tool of the present invention contains an oxidation accelerator having an iodine adsorption number of not more than 700 g/kg, in particular, in the exothermic composition; therefore, it is possible to reduce or prevent adsorption of the attractant by the oxidation accelerator. Therefore, it is possible to reduce or prevent the loss of attractant diffusion property or alteration of the attractant during the storage of the attracting tool as long as the attracting tool is stored without contact with oxygen; therefore, even after the attracting tool is stored for a long time, excellent attraction effects can be exhibited at the time of use. Further, with this property, the attracting tool is capable of diffusing an attractant for a longer period, compared with known tools, after the beginning of use. More specifically, the attracting tool of the present invention has an improved attractant diffusion property.

Further, in the attracting tool of the present invention, even when the attracting tool is stored for a long period of time while the attractant and the exothermic composition are in contact with each other, excellent attraction effects can be obtained upon usage. Accordingly, in the attracting tool of the present invention, the attractant and the exothermic composition can exist in a state of being in contact with each other, or can exist in a state of not being in contact with each other. Further, in the attracting tool of the present invention, when the attracting tool has a structure such that the attractant is disposed outside the container bag for the exothermic composition without being in direct contact with the exothermic composition, and the attracting tool thus structured is packaged and stored in an air-impermeable outer bag, the outer bag may be filled with aroma derived from the attractant. Even in this case, according to the attracting tool of the present invention, adsorption of the attractant that fills the outer bag by the oxidation accelerator in the exothermic composition can be reduced or prevented. Therefore, the present invention can provide attracting tools having various configurations that are not limited by the positional relationship between the attractant and the exothermic composition.

Further, the types of attractants to be used for such an attracting tool of the present invention are not limited, and any desired attractants can be widely used. Further, by using the oxidation accelerator having electrical conductivity equal to or higher than a certain level for the attracting tool of the present invention, the effects of the attracting tool can be exhibited more efficiently.

With such an attracting tool of the present invention, the desired attraction effects can be exhibited even when the amount of the attractant required for the attraction of animals is smaller than that in known tools, and even when the size of the attracting tool is smaller than known tools. Generally, in low-temperature environments, such as in winter or cold climates, the attractant diffusion property may decrease in some cases due to a decrease in ambient temperature. However, since the attracting tool of the present invention generates heat and thus is capable of increasing its temperature to be higher than the ambient temperature, it is possible to effectively diffuse an attractant even in a low-temperature environment.

Accordingly, the present invention also provides a method for attracting an animal, comprising the step of disposing the above-described attracting tool in a target area. The present invention further provides a method for producing an attracting tool with improved attractant diffusion, comprising the step of combining an oxidation accelerator having an iodine adsorption number of not more than 700 g/kg, an oxidizable metal powder, water, and an attractant. The present invention further provides a method for improving attractant diffusion of an attracting tool, comprising the step of combining an oxidation accelerator having an iodine adsorption number of not more than 700 g/kg, an oxidizable metal powder, water, and an attractant. The present invention further provides a method for improving attractant diffusion of an attracting tool comprising an attractant by using an exothermic composition containing an oxidation accelerator having an iodine adsorption number of not more than 700 g/kg, an oxidizable metal powder, and water. The present invention further provides use of an exothermic composition containing an oxidation accelerator having an iodine adsorption number of not more than 700 g/kg, an oxidizable metal powder, and water, for the production of an attracting tool comprising an attractant. The present invention further provides use of an exothermic composition containing an oxidation accelerator having an iodine adsorption number of not more than 700 g/kg, an oxidizable metal powder, and water, for improving attractant diffusion of an attracting tool comprising an attractant. In these inventions, the attracting tool, the exothermic composition, the components constituting them, such as the oxidation accelerator having an iodine adsorption number of not more than 700 g/kg, the oxidizable metal powder, water, and the attractant, their amounts, the production method, the application method, and other conditions are as described above.

EXAMPLES

The present invention is described below by referring to Examples. However, the present invention is not limited to these Examples.

Example 1

So as to evaluate attractant diffusion effects of an attracting tool, attracting tools 1 to 4 were produced in the following manner, and the concentrations of the components derived from the attractant diffused from each attracting tool were measured. Further, comparative attracting tool 1 as a Comparative Example was produced in the following manner, and the concentrations of the components derived from the attractant diffused from comparative attracting tool 1 were measured in the same manner.
(1) Production of Attracting Tools
Production of Attracting Tool 1
  Attracting tool 1 was produced in the following manner.
  The following components were used for the exothermic composition.
Exothermic Composition
  Iron Powder (produced by DOWA IP Creation Co., Ltd., product name: DKP, average particle diameter: 100 μm)
  Carbon Black (produced by Cabot Corporation; product name: Sho Black N550, iodine adsorption number: 43.6 g/kg, average particle diameter: 150 μm, electrically conductive)
  Water
  Vermiculite (average particle diameter: about 2.5 mm)
  Water-Absorbing Resin (acrylic acid polymer partial salt crosslinked product, average particle diameter: 250 μm)
  Common Salt
  Ethylenediaminetetraacetic Acid Trisodium Salt (produced by Kishida Chemical Co., Ltd., product name: Special-grade ethylenediaminetetraacetic acid trisodium salt (hydrate))
The following attractant was used.
Attractant
  Deer urine (produced by Tink's; product name: #69 Doe-In-Rut Buck Lure)

The components of the exothermic composition and the attractant were mixed, thereby obtaining a mixture. The proportions of iron powder, carbon black, water, vermiculite, water-absorbing resin, common salt, ethylenediaminetetraacetic acid trisodium salt, and the attractant were 55 wt %, 7.9 wt %, 18.8 wt %, 5.6 wt %, 2.2 wt %, 1.4 wt %, 0.1 wt %, and 9 wt %, respectively. The total amount of these components was 23 g. The resulting mixture was housed in an air-permeable container bag (outside: nylon non-woven fabric, inside: polyethylene-coated, weight per area: 45 g/m$^2$, produced by Tokai Aluminum Foil Co., Ltd.), and the container bag was sealed (90 mm×50 mm), thereby obtaining attracting tool 1. Then, attracting tool 1 was quickly housed in an air-impermeable outer bag.
Production of Attracting Tool 2
  Attracting tool 2 was produced in the same manner as attracting tool 1, except that carbon black having an iodine adsorption number of 155 g/kg was used instead of the carbon black used for attracting tool 1. Then, attracting tool 2 was quickly housed in an air-impermeable outer bag.
Production of Attracting Tool 3
  Attracting tool 3 was produced in the same manner as attracting tool 1, except that carbon black having an iodine adsorption number of 297.7 g/kg was used instead of the carbon black used for attracting tool 1. Then, attracting tool 3 was quickly housed in an air-impermeable outer bag.

Production of Attracting Tool 4

Attracting tool 4 was produced in the same manner as attracting tool 1, except that carbon black having an iodine adsorption number of 675 g/kg was used instead of the carbon black used for attracting tool 1. Then, attracting tool 4 was quickly housed in an air-impermeable outer bag.

Production of Comparative Attracting Tool 1

Comparative attracting tool 1 was produced in the same manner as attracting tool 1, except that carbon black having an iodine adsorption number of 1050 g/kg was used instead of the carbon black used for attracting tool 1. Then, comparative attracting tool 1 was quickly housed in an air-impermeable outer bag.

(2) Evaluation of Attracting Tools

Each of the attracting tools and the comparative attracting tool individually housed in outer bags was allowed to stand for 24 hours at room temperature (20° C.); thereafter, the attracting tools and the comparative attracting tool were individually placed in separate deodorization test bags (10L) at room temperature, and then the bags were hermetically sealed. Subsequently, air is sucked from each deodorization test bag, and 5 L of odorless nitrogen was added. Thereafter, each attracting tool was taken out by opening the outer bag inside the deodorization test bag. The concentrations of ammonia ($NH_3$) and triethyl amine (TEA) in each deodorization test bag were measured at time points of one hour, two hours, and four hours after the opening using a detector tube (produced by Gastec Corporation; product names: No. 3M and No. 180).

(3) Results

Table 1 shows the results.

TABLE 1

| | Iodine Adsorption Number | 1 h | | 2 h | | 4 h | |
|---|---|---|---|---|---|---|---|
| | | $NH_3$ | TEA | $NH_3$ | TEA | $NH_3$ | TEA |
| Attracting Tool 1 | 43.6 | 40 | 130 | 60 | 200 | 80 | 120 |
| Attracting Tool 2 | 155 | 35 | 100 | 40 | 120 | 50 | 150 |
| Attracting Tool 3 | 297.7 | 30 | 80 | 26 | 110 | 45 | 120 |
| Attracting Tool 4 | 675 | 10 | 36 | 15 | 40 | 20 | 60 |
| Comparative Attracting Tool 1 | 1050 | 0 | 0 | 0 | 0 | 0 | 0 |

As clearly shown in Table 1, in comparative attracting tool 1 produced by using activated carbon having a high iodine adsorption number, ammonia and triethyl amine were adsorbed, and thus were not detected. In contrast, in attracting tools 1 to 4 produced by using activated carbon having a low iodine adsorption number, ammonia and triethyl amine were diffused in the bags. Further, the diffusion of these substances was sufficiently maintained even four hours after the opening of the outer bag.

The results thus revealed that attracting tools 1 to 4 exhibited excellent attraction effects. The results revealed, in particular, that attracting tools 1 to 4 are capable of effectively diffusing an attractant even when the exothermic composition and the attractant coexist in contact with each other, and that therefore, attractant diffusion in these attracting tools was significantly higher than comparative attracting tool 1. Further, the results also revealed that even though attracting tools 1 to 4 were used at least 24 hours after their production, that is, even though the attracting tools had been stored with the attractant and the exothermic composition coexisting at least for 24 hours, they were capable of effectively diffusing the attractant.

Example 2

Attracting tools 1 to 4 and comparative attracting tool 1 produced in Example 1 were evaluated in terms of intensity of odor diffused from the attracting tool. More specifically, four test subjects smelled each attracting tool taken out from the outer bag in a temporal manner, and the odor intensities were evaluated (at room temperature 20° C.) using scales with equal intervals in which "odorless" was graded as 0, and "very strong odor" was graded as 10. The larger the odor intensity value, the greater the evaluation, i.e., the odor was strongly diffused. Table 2 shows the results.

TABLE 2

| | Subject | Iodine Adsorption Number | 0 h Sensory Score | (Avg.) | 1 h Sensory Score | (Avg.) | 2 h Sensory Score | (Avg.) | 4 h Sensory Score | (Avg.) |
|---|---|---|---|---|---|---|---|---|---|---|
| Attracting Tool 1 | A | 43.6 | 10 | 10.0 | 7 | 7.0 | 6 | 5.5 | 3 | 2.5 |
| | B | | 10 | | 8 | | 7 | | 4 | |
| | C | | 10 | | 8 | | 7 | | 4 | |
| | D | | 10 | | 7 | | 5 | | 2 | |
| Attracting Tool 2 | A | 155 | 6 | 6.0 | 3 | 3.5 | 2 | 2.5 | 1 | 1.5 |
| | B | | 5 | | 3 | | 2 | | 1 | |
| | C | | 6 | | 4 | | 2 | | 0 | |
| | D | | 6 | | 4 | | 3 | | 2 | |
| Attracting Tool 3 | A | 297.7 | 2 | 3.0 | 1 | 1.5 | 1 | 1.5 | 0 | 0.5 |
| | B | | 3 | | 2 | | 1 | | 1 | |
| | C | | 3 | | 1 | | 1 | | 0 | |
| | D | | 4 | | 2 | | 2 | | 1 | |
| Attracting Tool 4 | A | 675 | 1 | 1.0 | 1 | 0.5 | 0 | 0.0 | 0 | 0.0 |
| | B | | 2 | | 1 | | 0 | | 0 | |
| | C | | 2 | | 1 | | 0 | | 0 | |
| | D | | 1 | | 0 | | 0 | | 0 | |
| Comparative Attracting Tool 1 | A | 1050 | 0 | 0.0 | 0 | 0.0 | 0 | 0.0 | 0 | 0.0 |
| | B | | 0 | | 0 | | 0 | | 0 | |
| | C | | 0 | | 0 | | 0 | | 0 | |
| | D | | 0 | | 0 | | 0 | | 0 | |

As clearly shown in Table 2, the test subjects did not sense an odor from comparative attracting tool 1 produced by using activated carbon having a high iodine adsorption number. In contrast, the test subjects clearly sensed an odor from attracting tools 1 to 4 produced by using activated carbon having a low iodine adsorption number. The results thus revealed that attractant diffusion was significantly improved in attracting tools 1 to 4, and that attracting tools 1 to 4 were capable of exhibiting excellent attraction effects, compared with comparative attracting tool 1. Further, although the details are not shown, the attracting tools were also evaluated as to whether they sufficiently generated heat, with the result that their heat generation was sufficient and achieved a practical level.

Further, the results also revealed that attracting tools 1 to 4 were capable of exhibiting excellent attraction effects, even though the attractant was incorporated therein beforehand. It was thus revealed that attracting tools 1 to 4 were capable of exhibiting excellent attraction effects while sufficiently generating heat, and that therefore, they are useful for hunting. It was also revealed that attracting tools 1 to 4 are free from, for example, the trouble of adding an attractant to the device at the time of use, and that attracting tools 1 to 4 also do not cause an inconvenience such as adherence of the attractant to skin or clothing upon the addition.

Example 3

An outdoor test was performed using attracting tool 1 produced in Example 1 so as to confirm its effects of attracting hunting animals. Specifically, the test was performed in winter by placing a hunting stand on a tree, taking out two attracting tools 1 from respective outer bags to cause them generate heat, and placing the attracting tools 1 on the ground near the stand. Within 30 minutes after placement, three deer, which were attracted to the attracting tools 1, appeared. As demonstrated above, the attracting tool of the present invention attracted hunting animals in an actual outdoor environment, and was therefore confirmed to be useful for hunting.

Example 4

Attracting tools 5 to 12 detailed below were produced in the same manner as attracting tool 1. Attracting tools 5 to 12 all have the same excellent attraction effects as those of attracting tools 1 to 4.

Attracting Tool 5

Attracting tool 5 having the formulation below was produced in the same manner as attracting tool 1, except that a container bag having a size of 130 mm×95 mm was used. Then, attracting tool 5 was quickly housed in an air-impermeable outer bag. The unit is "wt %." The total amount of the components was 50 g.

| Iron powder | 55 |
| Carbon black | 7.9 |
| Vermiculite | 5.6 |
| Water-absorbing resin | 2.2 |
| Common salt | 1.4 |
| Water | 22.8 |
| Ethylenediaminetetraacetic acid trisodium salt | 0.1 |
| Deer urine | 5 |
| Total | 100 |

Attracting Tool 6

Attracting tool 6 having the formulation below was produced in the same manner as attracting tool 1. Shortly thereafter, attracting tool 6 was housed in an air-impermeable outer bag. The unit is "wt %." The total amount of the components was 23 g.

| Iron powder | 55 |
| Carbon black | 15 |
| Vermiculite | 5.6 |
| Water-absorbing resin | 2.2 |
| Common salt | 1.4 |
| Water | 15.7 |
| Ethylenediaminetetraacetic acid trisodium salt | 0.1 |
| Deer urine | 5 |
| Total | 100 |

Attracting Tool 7

Attracting tool 7 having the formulation below was produced in the same manner as attracting tool 1, except that wild boar urine (produced by Tink's; product name: Power Pig Lures) was used as the attractant. Then, attracting tool 7 was quickly housed in an air-impermeable outer bag. The unit is "wt %." The total amount of the components was 23 g.

| Iron powder | 55 |
| Carbon black | 7.9 |
| Vermiculite | 5.6 |
| Water-absorbing resin | 2.2 |
| Common Salt | 1.4 |
| Water | 17.8 |
| Ethylenediaminetetraacetic acid trisodium salt | 0.1 |
| Wild boar urine | 10 |
| Total | 100 |

Attracting Tool 8

Attracting tool 8 having the formulation below was produced in the same manner as attracting tool 1, except that artificial urine (produced by Tink's; product name: Power Moose Synthetic Cow Estrous) was used as the attractant, and a container bag having a size of 130 mm×95 mm was used. Then, attracting tool 8 was quickly housed in an air-impermeable outer bag. The unit is "wt %." The total amount of the components was 80 g.

| Iron powder | 55 |
| Carbon black | 7.9 |
| Vermiculite | 5.6 |
| Water-absorbing resin | 2.2 |
| Common salt | 1.4 |
| Water | 12.8 |
| Ethylenediaminetetraacetic acid trisodium salt | 0.1 |
| Artificial urine | 15 |
| Total | 100 |

Attracting Tool 9

Attracting tool 9 having the formulation below was produced in the same manner as attracting tool 1. Then, attracting tool 9 was quickly housed in an air-impermeable outer bag. The unit is "wt %." The total amount of the components was 23 g.

| Iron powder | 55 |
| Carbon black | 7.9 |

| | |
|---|---|
| Vermiculite | 5.6 |
| Water-absorbing resin | 2.2 |
| Common salt | 1.4 |
| Water | 7.8 |
| Ethylenediaminetetraacetic acid trisodium salt | 0.1 |
| Deer urine | 20 |
| Total | 100 |

Attracting Tool 10

Figure 1:
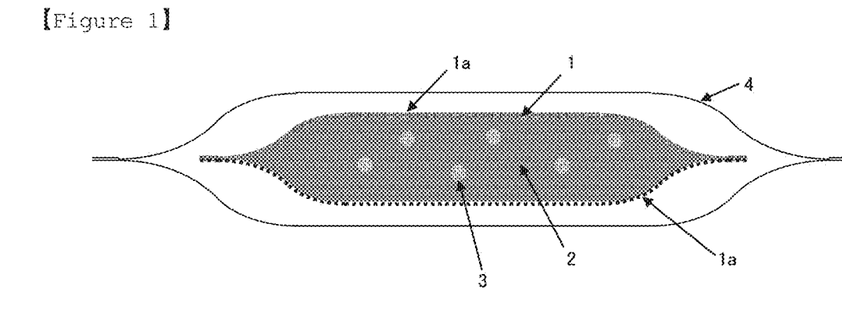
FIG. 1 is an example of an attracting tool packaged in an outer bag. The container bag shown in FIG. 1 is a model drawing of a container bag having air-permeable portions on both sides.
Figure 2:
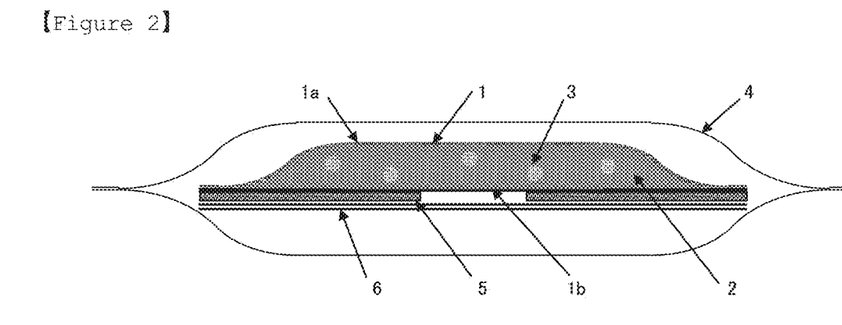
FIG. 2 is an example of a stick-on type attracting tool packaged in an outer bag. The air-permeable container bag shown in FIG. 2 is a model drawing of a container bag having an air-permeable portion on one side, and an air-impermeable portion on the other side.
Figure 3:
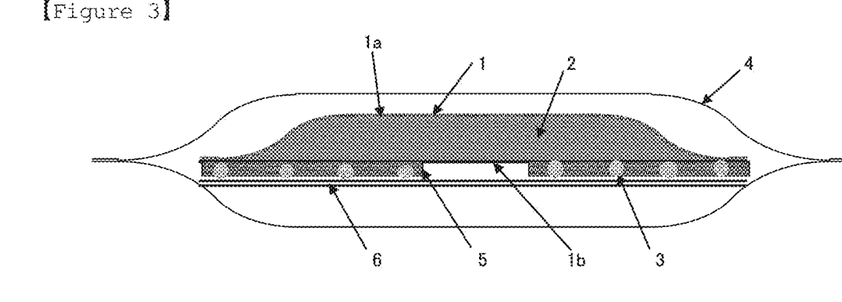
FIG. 3 is an example of a stick-on type attracting tool packaged in an outer bag. The air-permeable container bag shown in FIG. 3 is a model drawing of a container bag having an air-permeable portion on one side, and an air-impermeable portion on the other side.
Figure 4:
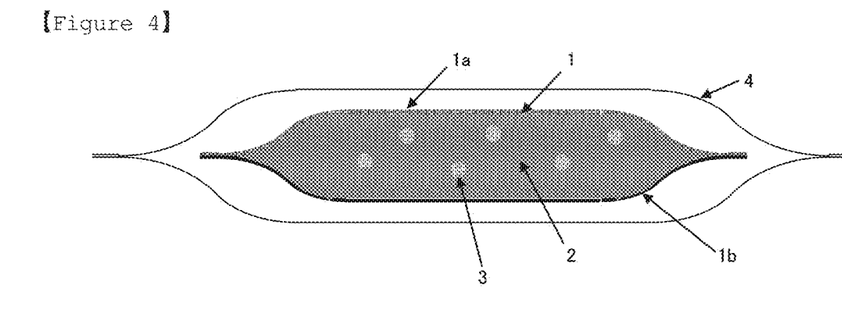
FIG. 4 is an example of an attracting tool packaged in an outer bag. The air-permeable container bag shown in FIG. 4 is a model drawing of a container bag having an air-permeable portion on one side, and an air-impermeable portion on the other side.

Attracting tool 10 having the formulation below was produced using the components in specified proportions below, as well as carbon black and activated carbon as oxidation accelerators. The adhesive container bag shown in FIG. 2 was used. Then, attracting tool 10 was quickly housed in an air-impermeable outer bag. The same activated carbon as that for comparative attracting tool 1 was used. The oxidation accelerator contained in attracting tool 10 had an iodine adsorption number of 100 g/kg. The unit is "wt %." The total amount of the components was 23 g.

| | |
|---|---|
| Iron powder | 55 |
| Carbon black | 7.5 |
| Activated carbon | 0.4 |
| Vermiculite | 5.6 |
| Water-absorbing resin | 2.2 |
| Common salt | 1.4 |
| Water | 17.8 |
| Ethylenediaminetetraacetic acid trisodium salt | 0.1 |
| Deer urine | 10 |
| Total | 100 |

Attracting Tool 11

Attracting tool 11 having the formulation below was produced using the components in specified proportions below, as well as carbon black and activated carbon as oxidation accelerators. The adhesive container bag shown in FIG. 2 was used. Then, attracting tool 11 was quickly housed in an air-impermeable outer bag. The same activated carbon as that used for comparative attracting tool 1 was used. The oxidation accelerator contained in attracting tool 11 had an iodine adsorption number of 100 g/kg. The unit is "wt %." The total amount of the components was 23 g.

| | |
|---|---|
| Iron powder | 65 |
| Carbon black | 5.83 |
| Activated carbon | 0.31 |
| Vermiculite | 4.36 |
| Water-absorbing resin | 1.71 |
| Common salt | 1.09 |
| Water | 13.84 |
| Ethylenediaminetetraacetic acid trisodium salt | 0.08 |
| Deer urine | 7.78 |
| Total | 100 |

Attracting Tool 12

Attracting tool 12 having the formulation below was produced in the same manner as attracting tool 1, except that carbon black and activated carbon were used as oxidation accelerators. Then, attracting tool 12 was quickly housed in an air-impermeable outer bag. The same activated carbon as that used for comparative attracting tool 1 was used. The oxidation accelerator contained in attracting tool 12 had an iodine adsorption number of 450 g/kg. The unit is "wt %." The total amount of the components was 23 g.

| | |
|---|---|
| Iron powder | 55 |
| Carbon black | 4.6 |
| Activated carbon | 3.3 |
| Vermiculite | 5.6 |
| Water-absorbing resin | 2.2 |
| Common salt | 1.4 |
| Water | 12.8 |
| Ethylenediaminetetraacetic acid trisodium salt | 0.1 |
| Deer urine | 15 |
| Total | 100 |

REFERENCE NUMERALS

1. Air-permeable container bag (1a is an air-permeable portion, and 1b is an air-impermeable portion)
2. Exothermic composition
3. Attractant
4. Air-impermeable outer bag
5. Adhesive
6. Release paper

The invention claimed is:

1. An attracting tool comprising an exothermic composition and an attractant, the exothermic composition containing an oxidation accelerator having an iodine adsorption number of not more than 160 g/kg, an oxidizable metal powder and water,
    wherein at least the exothermic composition is housed in an air-permeable container bag;
    wherein the attractant is contained in an amount of 0.1 to 25 parts by weight per 100 parts by weight of the exothermic composition;
    and wherein the attractant is contained in an amount of 0.1 to 500 parts by weight per 100 parts by weight of the oxidation accelerator in the exothermic composition.

2. The attracting tool according to claim 1, wherein the exothermic composition further contains a water-soluble salt, a water-retaining agent, and/or a metal ion sequestrant.

3. The attracting tool according to claim 1, wherein the proportion of the oxidation accelerator in the exothermic composition is 1 to 30 wt %.

4. The attracting tool according to claim 1, wherein the oxidation accelerator is at least one member selected from the group consisting of carbon black, graphite, activated carbon, coal, charcoal, bamboo charcoal, acetylene black, and waste coffee grounds charcoal.

5. The attracting tool according to claim 1, wherein the oxidation accelerator has electrical conductivity.

6. The attracting tool according to claim 1, wherein the attractant is housed in an air-permeable container bag.

7. The attracting tool according to claim 1, wherein the attractant is supported on a carrier.

8. The attracting tool according to claim 1, wherein the container bag is biodegradable and/or contains an oxidative degradation agent.

9. The attracting tool according to claim 2, wherein the proportion of the oxidation accelerator in the exothermic composition is 1 to 30 wt %.

10. An attracting tool comprising an exothermic composition and an attractant, the exothermic composition containing an oxidation accelerator having an iodine adsorption number of not more than 300 g/kg, an oxidizable metal powder and water, wherein the exothermic composition and the attractant are housed in an air-permeable container bag.

11. The attracting tool according to claim 10, wherein the exothermic composition further contains a water-soluble salt, a water-retaining agent, and/or a metal ion sequestrant.

12. The attracting tool according to claim 10, wherein the proportion of the oxidation accelerator in the exothermic composition is 1 to 30 wt %.

13. The attracting tool according to claim 10, wherein the attractant is contained in an amount of 0.1 to 25 parts by weight per 100 parts by weight of the exothermic composition.

14. The attracting tool according to claim 10, wherein the attractant is contained in an amount of 0.1 to 500 parts by weight per 100 parts by weight of the oxidation accelerator in the exothermic composition.

15. The attracting tool according to claim 10, wherein the oxidation accelerator is at least one member selected from the group consisting of carbon black, graphite, activated carbon, coal, charcoal, bamboo charcoal, acetylene black, and waste coffee grounds charcoal.

16. The attracting tool according to claim 10, wherein the oxidation accelerator has electrical conductivity.

17. The attracting tool according to claim 10, wherein the container bag is biodegradable and/or contains an oxidative degradation agent.

* * * * *